US012396649B2

(12) United States Patent
Spiegelberg et al.

(10) Patent No.: US 12,396,649 B2
(45) Date of Patent: Aug. 26, 2025

(54) DEVICE FOR DETERMINING A PARAMETER FOR DIAGNOSING HYDROCEPHALUS AND OTHER DISORDERS OF INTRACRANIAL PRESSURE

(71) Applicants: UNIVERSITÄT ZÜRICH, Zürich (CH); Andreas Spiegelberg, Horgen (CH)

(72) Inventors: Andreas Spiegelberg, Horgen (CH); Vartan Kurtcuoglu, Winterthur (CH)

(73) Assignees: Andreas Spiegelberg, Horgen (CH); Universitat Zurich, Zurich (CH)

( * ) Notice: Subject to any disclaimer, the term of this patent is extended or adjusted under 35 U.S.C. 154(b) by 1158 days.

(21) Appl. No.: 16/612,767

(22) PCT Filed: May 11, 2018

(86) PCT No.: PCT/EP2018/062262
§ 371 (c)(1),
(2) Date: Nov. 12, 2019

(87) PCT Pub. No.: WO2018/206799
PCT Pub. Date: Nov. 15, 2018

(65) Prior Publication Data
US 2020/0196884 A1 Jun. 25, 2020

(30) Foreign Application Priority Data

May 12, 2017 (DE) .................... 10 2017 004 576.3
Sep. 23, 2017 (EP) .................... 17192789
Jan. 12, 2018 (DE) .................... 10 2018 100 697.7

(51) Int. Cl.
*A61B 5/00* (2006.01)
*A61B 5/0205* (2006.01)
(Continued)

(52) U.S. Cl.
CPC ............ *A61B 5/031* (2013.01); *A61B 5/0205* (2013.01); *A61B 5/4064* (2013.01);
(Continued)

(58) Field of Classification Search
CPC ..... A61B 5/031; A61B 5/0205; A61B 5/7235; A61B 8/0808; A61B 8/485; A61B 5/024;
(Continued)

(56) References Cited

U.S. PATENT DOCUMENTS 6,387,051 B1 * 5/2002 Ragauskas ........... A61B 8/0808
600/442
2005/0015009 A1 1/2005 Mourad et al.
(Continued)

FOREIGN PATENT DOCUMENTS

WO WO-2007022288 A2 * 2/2007 ............. A61B 5/031

OTHER PUBLICATIONS

Jetzki et al. "Analysis of Pulse Waves in Intracranial Pressure" Proc of the 29 Ann Internat Conf of the IEEE EMBS Aug. 23-26, 2007, p. 2863-2866.

*Primary Examiner* — Joel Lamprecht
*Assistant Examiner* — James F McDonald, III
(74) *Attorney, Agent, or Firm* — JMB Davis Ben-David (57) ABSTRACT

The invention relates to a device for determining a parameter for the diagnostics of hydrocephalus and other disorders of intracranial pressure, wherein information about the volume elasticity is obtained from a pressure signal or another characteristic signal which contains information about the pressure or the volume composition in the skull.
The characteristic parameter determined according to the invention is the ratio of the amplitude of a modulating wave in the processed characteristic signal to the amplitude of the modulated wave in the course of the pulse amplitude of the modulated wave of the processed characteristic signal.

12 Claims, 7 Drawing Sheets

(51) Int. Cl.
*A61B 5/03* (2006.01)
*A61B 8/00* (2006.01)
*A61B 8/08* (2006.01)

(52) U.S. Cl.
CPC .......... *A61B 5/7235* (2013.01); *A61B 8/0808* (2013.01); *A61B 8/485* (2013.01); *A61B 5/6868* (2013.01)

(58) Field of Classification Search
CPC ..... A61B 5/053; A61B 5/0816; A61B 5/4064; A61B 5/6868
See application file for complete search history.

(56) References Cited

U.S. PATENT DOCUMENTS

| | | | |
|---|---|---|---|
| 2006/0079773 A1 | 4/2006 | Mourad et al. | |
| 2007/0287899 A1* | 12/2007 | Poupko | A61B 5/053 600/383 |
| 2011/0196245 A1* | 8/2011 | Poupko | A61B 5/02028 600/506 |
| 2013/0109979 A1* | 5/2013 | Poupko | A61B 5/021 600/506 |
| 2013/0223709 A1* | 8/2013 | Wagner | A61B 5/6814 382/128 |
| 2014/0371545 A1 | 12/2014 | Ben-Ari et al. | |
| 2017/0055839 A1* | 3/2017 | Levinson | A61B 5/7225 |

* cited by examiner

DEVICE FOR DETERMINING A PARAMETER FOR DIAGNOSING HYDROCEPHALUS AND OTHER DISORDERS OF INTRACRANIAL PRESSURE

CROSS-REFERENCE TO RELATED APPLICATIONS

This is the U.S. National Stage of International Patent Application No. PCT/EP2018/062262 filed on May 11, 2018, which claims priority to German Patent Application Nos. 10 2017 004 576.3 filed on May 12, 2017 and 10 2018 100 697.7 filed on Jan. 12, 2018, and European Patent Application No. 17192789.0 filed on Sep. 23, 2017.

The present invention relates to a device for determining a characteristic parameter for the diagnostics of hydrocephalus and other disorders of intracranial pressure and a method for determining a characteristic parameter of the head content of humans and other mammals.

For the diagnostics of patients who have an imbalance between the formation of cerebro-spinal fluid and the reabsorption of cerebro-spinal fluid, the so-called hydrocephalus patients, and also in other patients, in which the pressure conditions in the head or brain are disturbed, devices are used which determine the pressure or volume elasticity of the space in the skull. In many of these patients, the mean pressure in the cerebro-spinal fluid, is not pathologically elevated. However, their volume elasticity of the content of the skull is limited and smallest triggering pressure changes lead to wave-shaped increases in pressure, especially during sleep and when lying down. In others of these patients, the reduction in volume elasticity is also associated with an increase in pressure.

Volume elasticity is a measure of the ability of the brain to compensate for volume changes. The brain is trapped in the rigid bony cranial vault. In addition to the brain matter, arteries that deliver blood to the brain, veins that carry the blood away from the brain, and cerebro-spinal fluid chambers that contain the cerebro-spinal fluid (liquor cerebrospinalis) are present in this cavity. As the volume of one of these compartments increases, the volume of one or more of the other compartments must be displaced because the total volume of the rigid cranial vault is constant. In the healthy state, the volume elasticity is high enough for changes in the volume of one of the compartments, e.g. swelling of the brain matter due to injuries, to be compensated without significant pressure increase.

The volume elasticity (compliance) can be determined by an invasive procedure in which a catheter is inserted into the cerebro-spinal fluid space via a drill hole in the skull, a certain volume $\Delta V$ of a fluid is injected and the resulting pressure increase $\Delta p$ is measured. As a result, the compliance C is given by the equation $C=\Delta V/\Delta p$. In healthy people, the compliance is greater than 1 ml/mmHg.

Naturally, with each heartbeat, a certain volume of blood is supplied through the arteries, causing a pressure increase. This pressure increase can be measured with an invasive pressure probe. The blood volume delivered by the heartbeat is not known, so that the compliance cannot be calculated numerically. However, the experienced physician receives an indication of the compliance from the pulse amplitude of the intracranial pressure (ICP).

For direct measurement of intracranial pressure, miniaturized pressure transducers are used, which are introduced invasively into the cranial vault. Such pressure transducers are designed as semiconductor sensors (for example according to DE000002206624) or as fiber-optic sensors (for example according to U.S. Pat. No. 4,787,396). Like the determination of the compliance from volume injection, the direct measurement of intracranial pressure is a very invasive procedure which represents a great burden and risk for the patient.

Because of the disadvantages of direct measurements, attempts have been made in various ways to noninvasively determine intracranial pressure and/or compliance "externally".

Paulat (DE000019606687A1) describes the detection of the electrical impedance of the skull with two or more electrodes attached to the scalp. The course of the impedance is influenced by the ratio of the compartments blood, brain matter, and cerebro-spinal fluid periodically at each heartbeat and a graph with periodic portions is obtained. In this graph characteristic points (landmarks) are recognizable, the amplitude of which is described as characteristic for the ICP. However, this relationship changes from patient to patient under the influence of many factors, so that a reliable diagnostic procedure could not be developed from it.

Yost (U.S. 67/377,3407) describes a method in which the transit time of an ultrasonic signal through the skull is determined. The speed at which the impulse passes through the cranial vault is influenced by the different velocities of sound in the compartments and their composition. However, since the calibration of this procedure is uncertain and the relationship between the measurement results and the variable to be measured is changed from patient to patient due to a variety of factors, a reliable diagnostic procedure could not be developed from this.

Ben-Ari (WO 20141167418) proposes to obtain from the electrical capacitance and/or impedance of the head a parameter for possible edema (water accumulation in the tissue) in the interior of the head. Also due to the difficult calibration and the large interindividual differences, this procedure could not prevail.

Furthermore, US 2014/0371545 A1 describes a cerebrohemodynamic measuring device with at least one processor.

Furthermore, US 2005/0015009 A1 describes a method for determining the ICP of a subject on the basis of at least two variable inputs.

Furthermore, S. Jetzki, M. Kiefer, R. Eymann, M. Walter, and S. Leonhardt [1] mention the so-called PA-PM slope in connection with the dynamic course of intracranial pressure (ICP).

For some time, characteristic parameters have been used that are calculated from the ratio of all spontaneous changes in pulse amplitude to all spontaneous changes in mean intracranial pressure, see e.g. also the parameter RAP in [2], or the parameter AMP/P in [3] or the parameter RPPC in [4].

Common to the prior art [1]-[4] is, however, that all changes in the pulse amplitude are correlated with all changes in the mean pressure. The causes of changes in the pulse amplitude can be:
 change in the pulse amplitude of the arterial pressure pulse,
 change of compliance (compliance of the head content) by changes in volume of the cerebro-spinal fluid,
 change in compliance by changes in intracranial blood volume by altering the diameter of the arteries. (The brain regulates its blood flow by contracting or dilating the arteries in response to blood pressure. This mechanism is called autoregulation. Furthermore, the brain regulates its circulation by contracting or dilating the arteries in response to demand. This mechanism is called metabolic coupling.), changes in pulse amplitude by changes of the pressure and thus the compliance by respiration.

The causes of changes in mean pressure are also manifold:
- change in pressure due to hydrostatic effect when the position changes (lying, sitting, standing),
- change in pressure due to changes in cerebro-spinal fluid volume,
- change in pressure due to changes in intracranial blood volume by altering the diameter of the arteries (auto-regulation, metabolic coupling),
- changes in pressure due to respiration.

Since all these changes of pulse amplitude and pressure are correlated with each other in the above-cited methods, the correlation coefficients are low in the clinical routine and the parameters have little significance. None of the described systems for noninvasive diagnosis of hydrocephalus has hitherto proven itself in practice.

The object of the present invention is therefore to provide a device for diagnostics of hydrocephalus and other disorders of the intracranial pressure in which from a pressure signal or another characteristic signal which contains information about the pressure or the volume composition in the skull, information about the volume elasticity is obtained.

The invention takes advantage of the fact that due to the heartbeat and the respiration and other naturally occurring periodic events, periodic pressure fluctuations occur in the ICP. It was surprisingly found that it is possible to calculate from the relationships of these pressure fluctuations dimensionless parameters that are characteristic for the compliance. A characteristic parameter RAQ that is determined according to the invention is for example the ratio of the amplitude $A_{rp}$ of the respiratory waves in the pressure signal to the amplitude of the respiratory waves $AA_{vp}$ in the course of the heartbeat-induced pulse amplitude $A_{vp}$.

From the above-mentioned values, it is also possible according to the invention to calculate alternative characteristic parameters or output values, in particular dimensionless parameters, in particular in the form of quotients or in the form of parameters comprising such quotients. The calculation of a characteristic parameter or output value according to the invention is preferably carried out using at least one or more of the variables: $A_{vp}$, $A_{rp}$, $AA_{vp}$. Possibly other quantities may be used to determine the characteristic parameter (such as for example heart rate and/or respiratory rate). Of course, a characteristic parameter according to the invention can be scaled or by addition or subtraction be shifted appropriately. In particular, the characteristic parameter can be a dimensionless parameter by means of a suitable proportionality constant.

Figure 1:
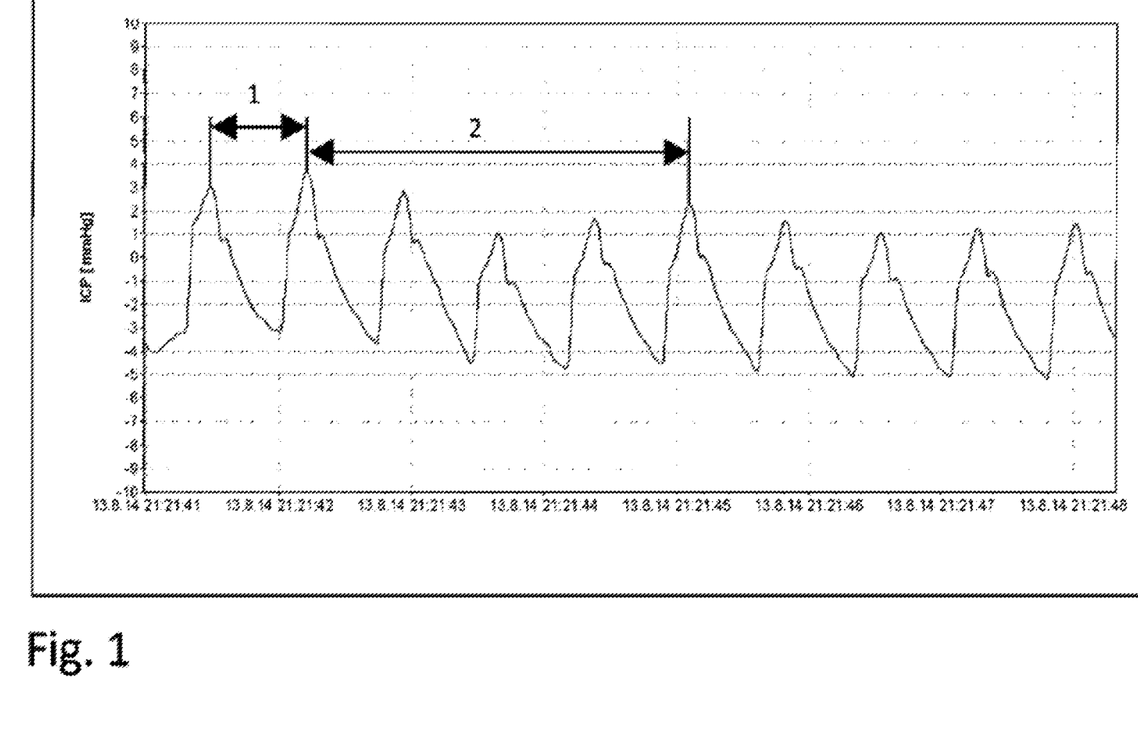
FIG. 1 is a representation of the course of intracranial pressure with a cardiac cycle 1 and a breathing cycle 2.

As described below by way of example, the processed characteristic signal may be the directly measured pressure signal. It can also be an impedance, capacitance, or other signal. Determined is, for example the amplitude of the pulse caused by the volume of blood supplied through the arteries at each heartbeat. Furthermore, the—lower-frequency—pressure wave is determined, which is caused by the fact that the blood outflow is periodically built up with each breath, which also corresponds to a change in volume, which is reflected in a pressure change. Since the periodic respiratory pressure change also causes the compliance to decrease and increase periodically, respiration also manifests itself in a modulation of the amplitude of the heartbeat-related pulse. In the ICP pressure graph, the pulsations caused by the heartbeat and respiration are recognizable and measurable. FIG. 1 schematically shows the course of the intracranial pressure with a cardiac cycle 1 and a respiratory cycle 2.

Whereas breathing modulates the heartbeat-related higher-frequency pulse amplitude in the frequency range of the respiratory rate (10 per minute to 20 per minute), other periodic influences modulate the amplitude of the heartbeat-related pulse wave (and other higher-frequency periodic waves) in other frequency ranges: A waves in the range of less than 1 per 3 minutes. B waves (resonance-oscillations of the regulation of the blood circulation, the so-called auto-regulation) in the range of ⅓ per minute to 3 per minute. C waves in the range of 3 per minute to 9 per minute. Each of the amplitudes of said periodic waves is modulated by the respective lower frequency waves. In the following, the terms "modulated wave" and "modulating wave" are used. Thus, when the amplitude of the heartbeat-related pulses is modulated by respiratory waves, the heartbeat-related pulses are the modulated wave and the respiratory waves are the modulating wave. The following illustrations are for better understanding related to the modulation of the amplitude of the heartbeat-related pulse wave through the respiratory wave. However, they are also applicable to any other combination of modulating and modulated wave with a corresponding change in the frequency-determining components.

The ratio RAQ of the amplitude $A_{rp}$ of the respiratory waves in the processed characteristic signal to the amplitude $AA_{vp}$ of the respiratory waves in the course of the heartbeat-induced pulse amplitude $A_{vp}$ of the evaluated signal is a ratio calculated by the equation $RAQ=A_{rp}/AA_{vp}$. It is independent of the calibration. Therefore, the device according to the invention is particularly suitable for the evaluation of non-invasively obtained signals containing information about the pressure or the volume composition or the volume elasticity in the skull. In this way, it is possible for the first time to obtain information about intracranial compliance in a non-invasive manner from uncalibrated signals. Furthermore, it is possible for the first time to obtain information about the intracranial compliance from the invasively directly measured pressure signal without having to inject a substance.

According to the invention, there is provided, in particular, a device for determining a characteristic parameter of the head content of humans and other mammals, which is suited for obtaining and evaluating a signal characteristic of the head content as an input variable, the device being configured to:
a. calculate the pulse amplitude $A_{vp}$ of each individual period (or half period) of a modulated wave of the characteristic signal and generate a signal $A_{vp}$ or a time series $A_{vp}$,
b. calculate the mean value MICP for each single period (or half period) of the modulated wave of the characteristic signal and generate a signal MICP or a time series MICP,
c. calculate the amplitude $A_{rp}$ of a modulating wave in the time series MICP or in the signal MICP,
d. calculate the amplitude $AA_{vp}$ of the modulating wave in the time series $A_{vp}$ or in the signal $A_{vp}$,
e. calculate the characteristic parameter as an output value using at least one or more of the quantities: $A_{vp}$, $A_{rp}$, $AA_{vp}$.

According to an embodiment of the invention, the characteristic parameter is a dimensionless parameter.

The solution according to the invention thus eliminates in particular the weakness of the above-cited approaches [1] to [4], in that only one influence (for example respiration) is taken into account both in the change of the pulse amplitude and in the change of the mean pressure (MICP). In particular, only the changes in the amplitude of a modulated wave in a narrow frequency band and the changes in the amplitude of a modulating wave in the same narrow frequency band are considered. For example, in a highly selective fashion, both in the numerator, and in the denominator of the quotient RAQ, only periodic changes in the same narrow frequency range are considered.

When applied according to the invention to the respiratory wave as a modulating wave and the pulse wave as a modulated wave, for example only the changes of the pulse amplitude in the respiratory frequency range as a modulated wave and the changes of the mean pressure in the respiratory frequency range as a modulating wave are taken into account. Due to the narrow-band limitation to for example the respiratory frequency range, both in the numerator and in the denominator only one influence is considered, whereas fluctuations caused by changes in position, autoregulation etc. are filtered out.

The above-mentioned step a) is therefore to be understood in particular such that the pulse amplitude $A_{vp}$ of each individual period (or half-period) of precisely one or only one modulated wave of the characteristic signal is calculated and a signal $A_{vp}$ or a time series $A_{vp}$ is generated.

Furthermore, according to the above-mentioned step c), it is therefore to be understood in particular that the amplitude $A_{rp}$ of precisely one or only one modulating wave in the time series MICP or in the signal MICP is calculated.

Furthermore, according to an embodiment of the invention, the parameter is a quotient or comprises a quotient.

Furthermore, according to an embodiment of the invention, the parameter is a quotient comprising the values $A_{rp}$ and $AA_{vp}$.

Furthermore, according to an embodiment of the invention, the parameter is a quotient comprising the size HF and/or AF, where HF is the heart rate and AF is the respiratory rate.

Furthermore, according to an embodiment of the invention, the quotient RAQ is proportional to or equal to one of the following expressions: $A_{rp}/AA_{vp}$, $Arp/(AA_{vp}/AF)$, $A_{rp}/(AA_{vp}*HF)$, $A_{rp}/(AA_{vp}*(HF/AF))$.

Furthermore, according to an embodiment of the invention, the characteristic signal is the directly measured pressure inside the head (ICP).

Furthermore, according to an embodiment of the invention the characteristic signal is the electrical impedance of the skull, which can be obtained by means of electrodes externally attachable to the skull.

Furthermore, according to one embodiment of the invention, it is provided that the characteristic signal is the electrical capacity of the skull, which can be obtained by means of electrodes which can be attached externally to the skull.

The device according to the invention can comprise said electrodes, these possibly being connected to the unit or units of the device according to the invention, so that the said impedance or capacity can be processed by means of the device.

Furthermore, according to an embodiment of the invention, the characteristic signal is the transit time of an ultrasound signal which is passed through the skull.

Furthermore, according to an embodiment of the invention, the characteristic signal is the transit time of an ultrasound signal which is reflected from the interior of the skull.

Furthermore, according to an embodiment of the invention, the device comprises one or more units which are or are configured for the purpose to
  a. calculate the pulse amplitude $A_{vp}$ of each individual period (or half period) of the modulated wave of the characteristic signal and generate a signal $A_{vp}$ or a time series $A_{vp}$ (3),
  b. calculate the mean value MICP for each individual period (or half period) of the modulated wave of the characteristic signal and generate a signal MICP or a time series MICP (4),
  c. calculate the amplitude $A_{rp}$ of a modulating wave in the time series MICP or in the signal MICP (5),
  d. calculate the amplitude $AA_{vp}$ of the modulating wave in the time series $A_{vp}$ or in the signal $A_{vp}$ (6),
  e. calculate the characteristic parameter as an output value using at least one or more of the quantities: $A_{vp}$, $A_{rp}$, $A_{vp}$.

In particular, for each of the above-mentioned calculations or steps a to e, a separate unit may be provided. However, it is also conceivable that the individual calculations/steps are performed by one unit or by several units to which the calculations are suitably distributed. Of course, the unit which carries out the calculation of the characteristic parameter can also carry out all other variants of the parameter calculation disclosed herein.

Furthermore, according to an embodiment of the invention, the respective unit which carries out the calculation of the characteristic parameter is an analogue computing circuit, a digital arithmetic circuit or a program-controlled microprocessor circuit.

According to one embodiment, the modulated wave may be one of the periodic waves from the group of B waves (⅓ period per minute to 3 periods per minute), C waves (3 periods per minute to 9 periods per minute), respiratory waves (10 Periods per minute to 20 periods per minute), heartbeat-related waves (20 periods per minute to 240 periods per minute).

Furthermore, according to one embodiment, the modulating wave may be one of the periodic waves from the group of A-waves (<1 per 4 minute), B-waves (⅓ per minute to 3 per minute), C-waves (3 per minute to 9 per minute), respiratory waves (10 per minute to 20 per minute), provided it has a lower frequency than the modulated wave.

According to another embodiment, a device is disclosed configured to calculate said characteristic parameter as a first output value and additionally configured to calculate a further characteristic parameter as a second output value, wherein for calculating the further output value in particular a combination of modulated and modulating waves is used, which differs from the combination of modulated and modulating wave used to calculate the characteristic parameter or first output value, wherein her the device is configured to form the quotient of the first output value and the second output value as a characteristic parameter of the head content.

In this embodiment, the device can comprise for example two devices according to the invention, wherein one device calculates the first output value and the other device calculates the second output value. The device then calculates said quotient from the first and the second output values.

Furthermore, according to an embodiment, the device is configured to form the time series $A_{vp}$ by using for the time period between a local maximum and the subsequent local minimum of the modulated wave of the characteristic signal, the difference between the local maximum and the local minimum as value for the time series $A_{vp}$, and by using for the ensuing time period between the local maximum and the subsequent local minimum of the modulated wave of the characteristic signal, the difference between the local maximum and the subsequent local minimum as value of the time series $A_{vp}$.

Furthermore, according to an embodiment, the device is configured to form the time series MICP by using for the time period between a local minimum and the subsequent local maximum of the modulated wave of the characteristic signal, the mean value between the local maximum and the local minimum as value for the time series MICP, and by using for the following time period between the local maximum and the subsequent local minimum of the modulated wave of the characteristic signal, the mean value between the local maximum and the subsequent local minimum as value of the time series MICP.

Another aspect of the present invention relates to a method for determining a characteristic parameter of the head content of humans and other mammals, in particular using a device according to the invention, comprising the steps:

a. calculating the pulse amplitude $A_{vp}$ of each individual period (or half-period) of a modulated wave of the characteristic signal and generating a signal $A_{vp}$ or a time series $A_{vp}$ (3),
b. calculating the mean value MICP for each individual period (or half period) of the modulated wave of the characteristic signal and generating a signal MICP or a time series MICP (4),
c. calculation of the amplitude $A_{rp}$ of a modulating wave in the time series MICP or in the signal MICP (5),
d. calculating the amplitude $AA_{vp}$ of the modulating wave in the time series $A_{vp}$ (6),
e. calculation of the characteristic using at least one or more of the following variables: $A_{vp}$, $A_{rp}$, $AA_{vp}$.

According to an embodiment of the method according to the invention, the characteristic parameter is a dimensionless parameter.

Furthermore, according to one embodiment of the method according to the invention, the characteristic parameter is a quotient or comprises a quotient.

Furthermore, according to an embodiment of the method according to the invention, the characteristic parameter is a quotient comprising the values $A_{rp}$ and $AA_{vp}$.

Furthermore, according to an embodiment of the method according to the invention, the characteristic parameter is a quotient comprising the quantity HF and/or AF, where HF is the heart rate and AF is the respiratory rate.

Furthermore, according to an embodiment of the method according to the invention, the quotient RAQ is proportional to or equal to one of the following expressions: $A_{rp}/AA_{vp}$, $A_{rp}/(AA_{vp}/AF)$, $A_{rp}/(AA_{vp}*HF)$, $A_{rp}/(AA_{vp}*(HF/AF))$.

Furthermore, according to an embodiment of the method according to the invention, the characteristic signal is the directly measured pressure in the cranial vault.

Furthermore, according to an embodiment of the method according to the invention, the characteristic signal is the electrical impedance of the skull, which is obtained by means of electrodes attached to the outside of the skull.

Furthermore, according to an embodiment of the method according to the invention, the characteristic signal is the electrical capacitance of the skull, which is obtained by means of electrodes attached to the outside of the skull.

Furthermore, according to an embodiment of the method according to the invention, the characteristic signal is the transit time of an ultrasound signal which is conducted through the skull.

Furthermore, according to an embodiment of the method according to the invention, the characteristic signal is the transit time of an ultrasonic signal that is reflected from inside the skull.

Furthermore, according to an embodiment of the method according to the invention, the time series $A_{vp}$ is formed by using for the time period between a local minimum and the subsequent local maximum of the modulated wave of the characteristic signal, the difference between the local maximum and the local minimum as value for the time series $A_{vp}$ and by using for the following time period between the local maximum and the subsequent local minimum of the modulated wave of the characteristic signal, the difference between the local maximum and the subsequent local minimum as value of the time series $A_{vp}$.

Furthermore, in the method according to the invention, two devices according to the invention can also be used (see above) or two output values can be calculated, wherein the first device or output value is characterized by a specific combination of modulated and modulating wave, and wherein the second device or output value is characterized by another combination of modulated and modulating wave, and wherein the characteristic parameter of the head content is formed by the quotient of the first output value and the second output value. In particular, all the combinations or examples described herein may be used for the said combinations of modulated and modulating waves.

Further features, embodiments and advantages of the present invention will be explained below with reference to Figures.

Figure 2:
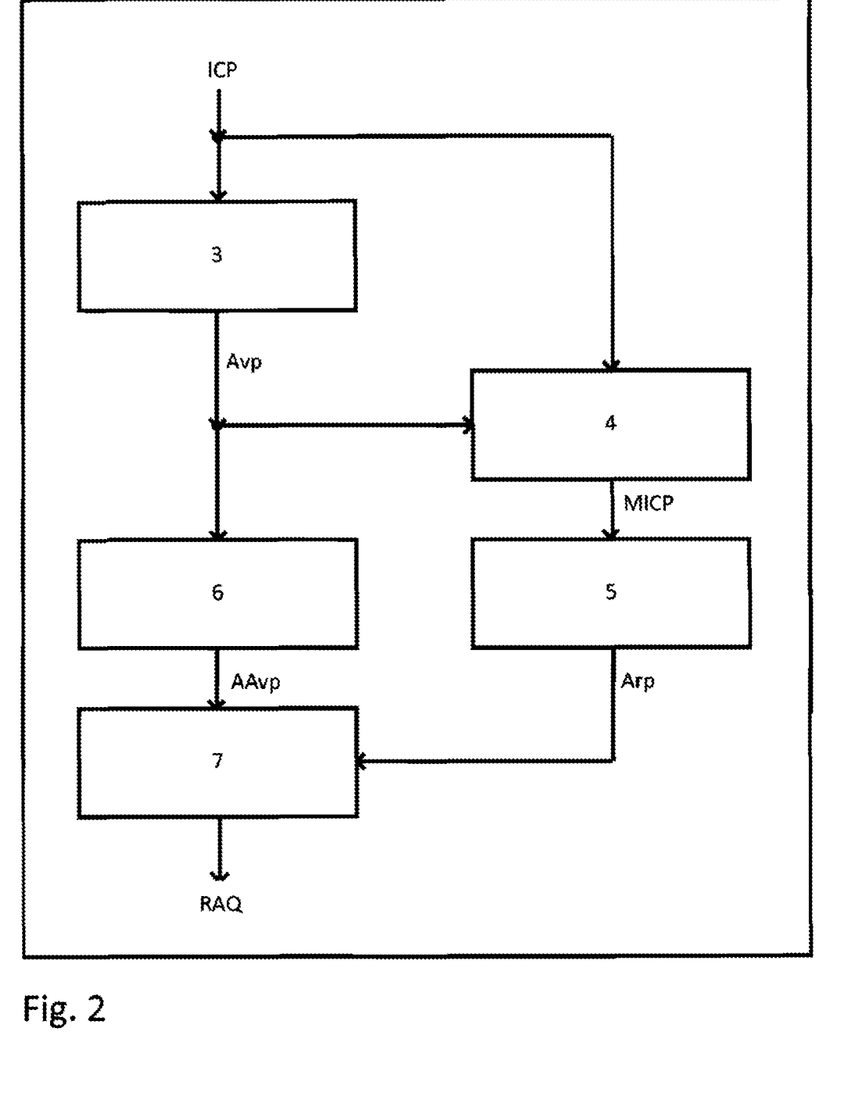
FIG. 2 shows a block diagram of a device according to the invention or of a method according to the invention.

A device according to the invention or a method according to the invention are shown schematically in FIG. 2.

According to an embodiment of the invention, the device, as shown in FIG. 2 by way of example for the processing of the ICP as a block diagram, consists of a processing unit for an invasive or noninvasively obtained characteristic signal which contains units for the following evaluations:

a. calculation of the pulse amplitude $A_{vp}$ of each individual heartbeat in the characteristic signal and generation of a signal $A_{vp}$ or a time series $A_{vp}$ (3),
b. calculation of the mean value MICP of the characteristic signal for each individual heartbeat and generation of a signal MICP or a time series MICP (4),
c. calculation of the amplitude $A_{rp}$ of the respiratory wave in the generated signal MICP or in the time series MICP (5),
d. calculation of the amplitude $AA_{vp}$ of the respiratory wave in the generated signal $A_{vp}$ or in the time series $A_{vp}$ (6),
e. calculation of the quotient of the parameter as a quantity RAQ which is proportional to RAQ=$A_{rp}/AA_{vp}$ (7), or calculation of the parameter in the form of the quotient RAQ, where RAQ=$A_{rp}/AA_{vp}$ (7).

In this embodiment of the invention, the heartbeat induced wave is the modulated wave and the respiratory wave is the modulating wave. Similarly, any combination of higher frequency modulated wave and lower frequency modulating wave is possible.

It has surprisingly been found that the calculation of the pulse amplitude $A_{vp}$ as the mean value of the difference between two local maxima of the modulated wave of the characteristic signal and the local minimum of the modulated wave of the characteristic signal between these two maxima leads to systematically distorted amplitude values by the modulating wave.

Therefore, in order to calculate the pulse amplitude $A_{vp}$ in the present invention, the difference between the local maximum and the local minimum is preferably selected as the value for the time series $A_{vp}$ for the time period between a local minimum and the subsequent local maximum of the modulated wave of the characteristic signal and for the subsequent period between the local maximum and the subsequent local minimum, the difference between the local maximum and the following local minimum is preferably selected. This will be explained below by way of example with reference to FIG. 3C.

Since the heart's stroke volume decreases with increasing heart rate at the same blood flow, it is provided according to an embodiment of the invention, that in the characteristic parameter or in the quotient RAQ the amplitude $AA_{vp}$ is multiplied by the heart rate or by a variable derived therefrom, so that the parameter RAQ is proportional to $$A_{rp}/(AA_{vp}*HF),$$

or so that the parameter RAQ is given by $$RAQ=A_{rp}/(AA_{vp}*HF),$$

where HF is the heart rate. This makes RAQ independent of the heart's stroke volume.

Furthermore, according to an embodiment of the invention, the respiratory frequency AF can also be included in the processing (because at high respiratory rates the rate of change per time is higher). Accordingly, it is possible to correct the characteristic parameter or the said quotient RAQ by the respiratory frequency by dividing the amplitude $AA_{vp}$ by the respiratory frequency AF or dividing it by a variable derived from the respiratory frequency AF in the calculation of the characteristic parameter or quotient RAQ.

Accordingly, then the parameter RAQ is proportional to $$A_{rp}/(AA_{vp}/AF)$$

or results in a quotient $$RAQ=A_{rp}/(AA_{vp}/AF).$$

As a result, the characteristic parameter or the quotient RAQ is independent of the respiratory rate.

Of course, the two above-mentioned correction options can also be combined according to a further embodiment. The characteristic parameter (here the quotient RAQ) is then calculated as $$RAQ=A_{rp}/(AA_{vp}*(HF/AF)),$$

or is proportional to $A_{rp}/(AA_{vp}*(HF/AF))$.

If necessary, the above-mentioned equations for calculating RAQ can contain a proportionality factor on the right-hand side, particularly so that, if necessary, the calculated characteristic parameter or the quotient RAQ is dimensionless. This is particularly the case when correcting only with the quantity HF or AF, each having the dimension of a frequency.

If the respiratory frequency AF and/or the heart rate is used to determine the characteristic parameter, the device according to the invention can comprise a unit for measuring the heart rate and/or a unit for measuring the respiratory rate.

In the calculation of the quotient RAQ according to the exemplary embodiment of FIG. 2, multiplying the value $AA_{vp}$ by the heart rate HF and/or dividing by the respiratory rate can be carried out after step 6, that is after the determination of $AA_{vp}$.

FIGS. 3A to 3J also show, by way of example for the processing of the ICP, how the individual values are determined from the pressure signal.

Figure 3A:
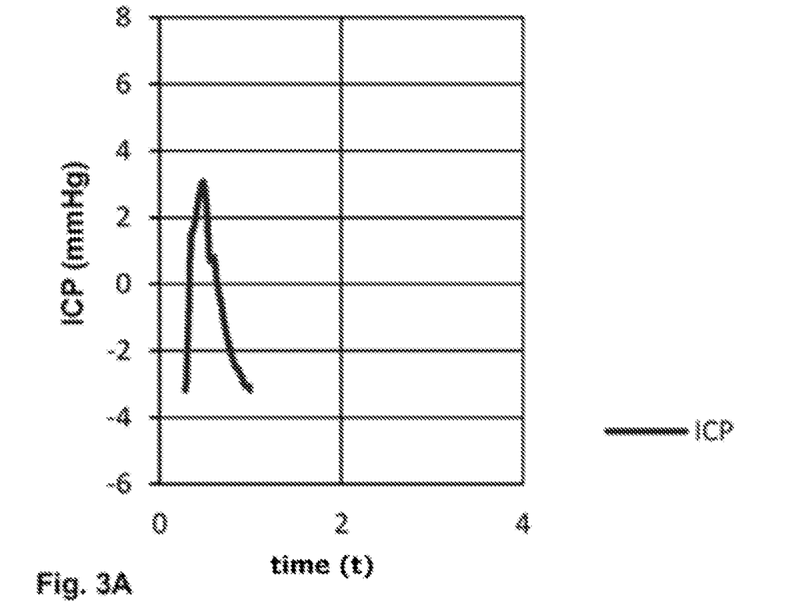
FIGS. 3A-3J show by way of example the processing of the pressure signal ICP in the context of the present invention.
Figure 3B:
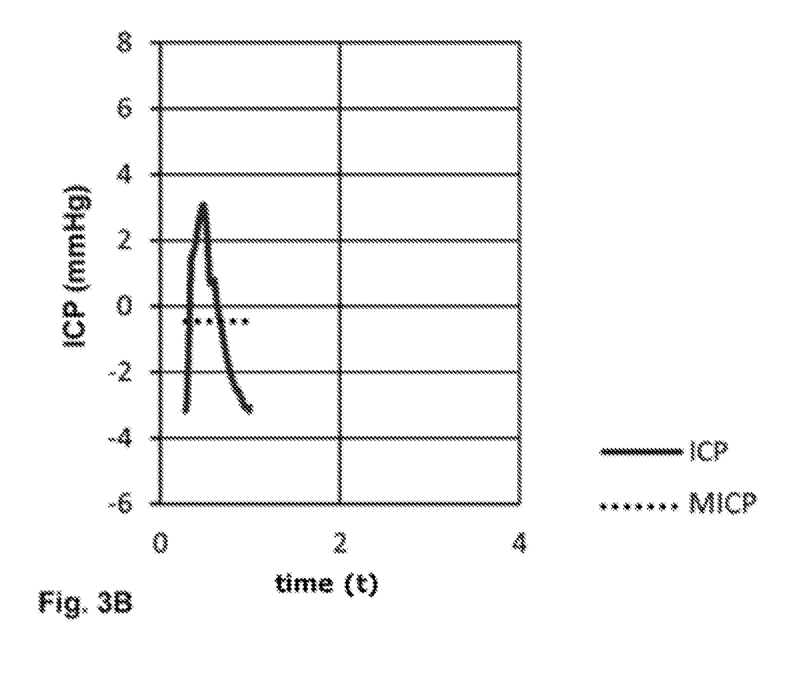
Figure 3C:
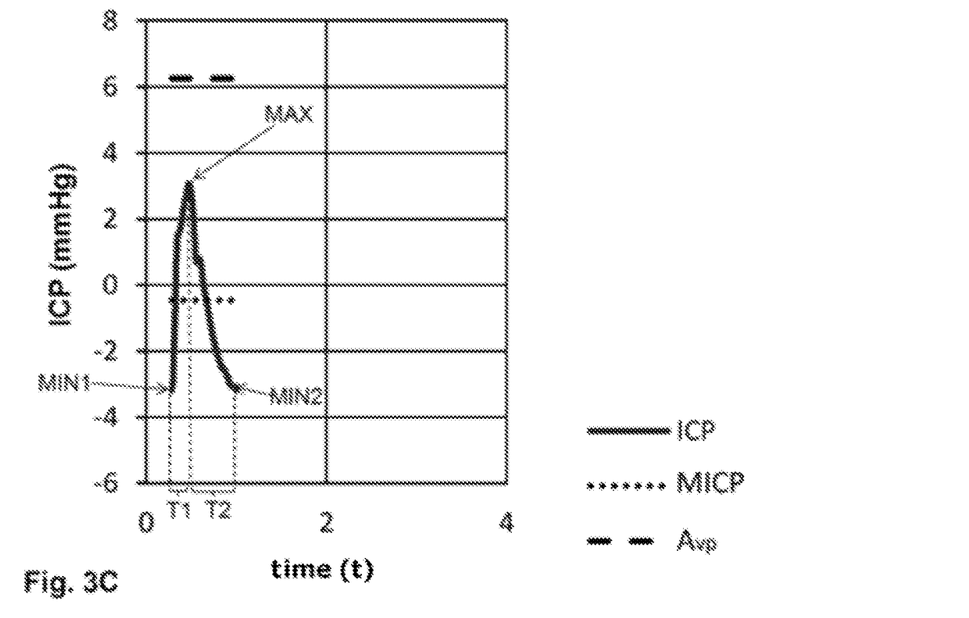
Figure 3D:
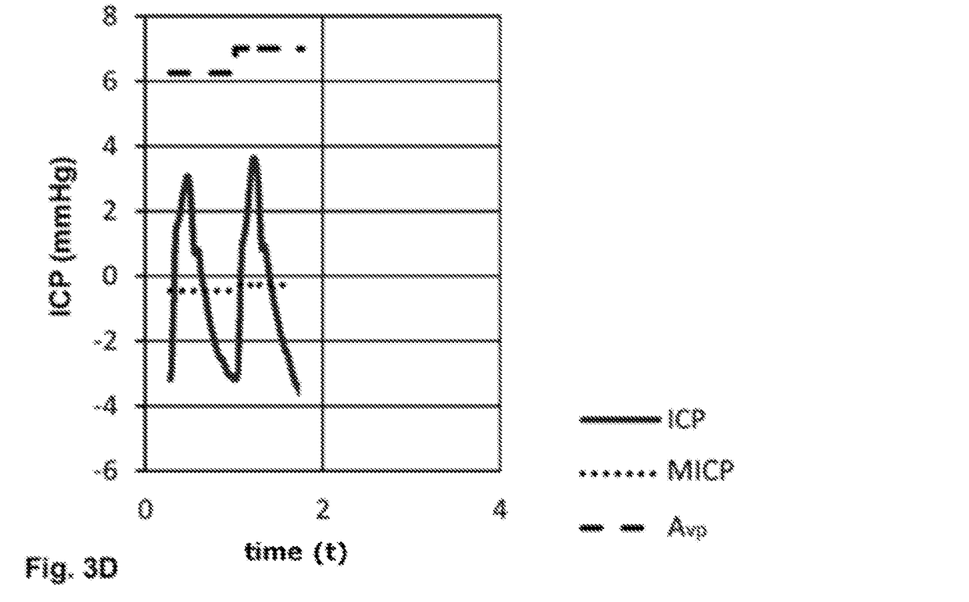
Figure 3E:
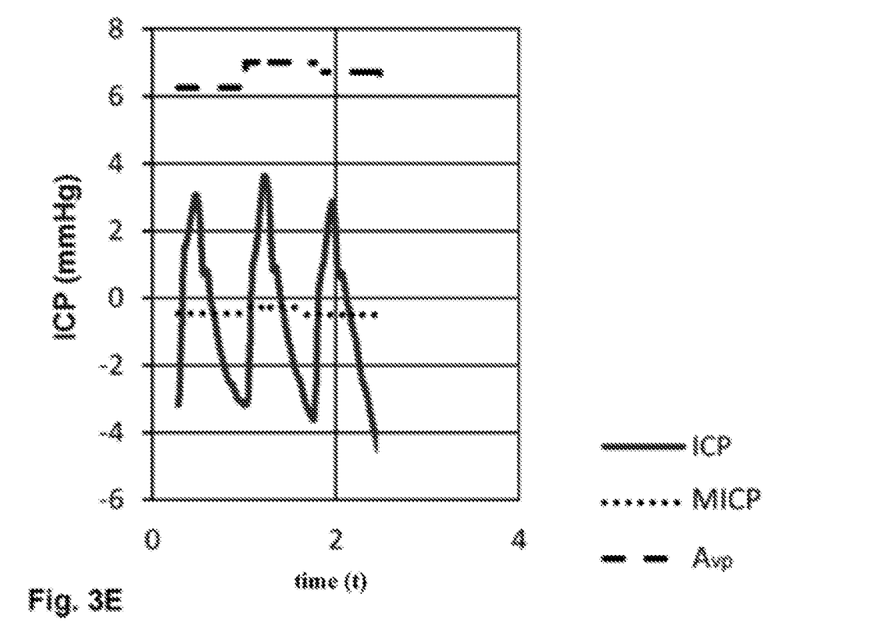
Figure 3F:
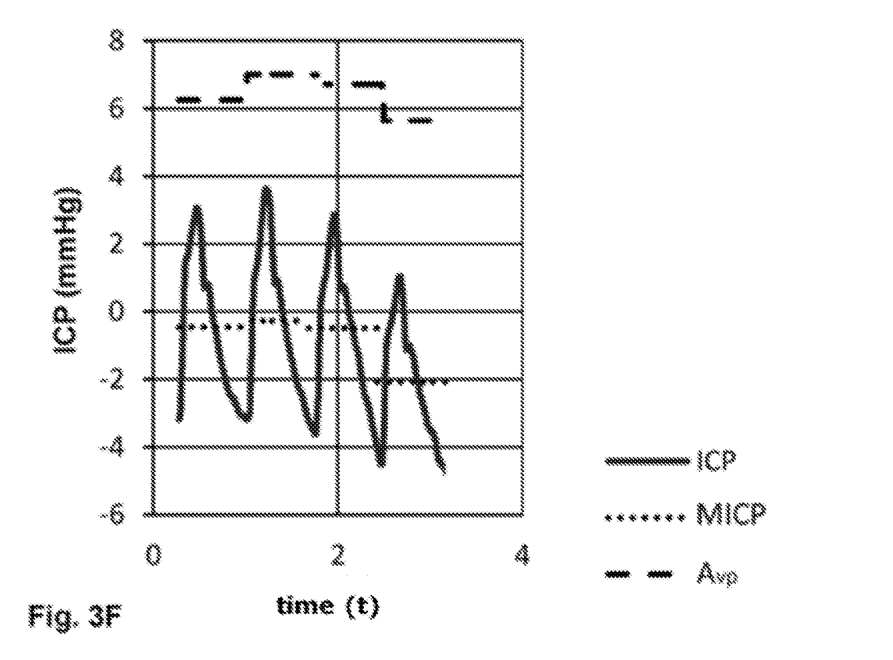
Figure 3G:
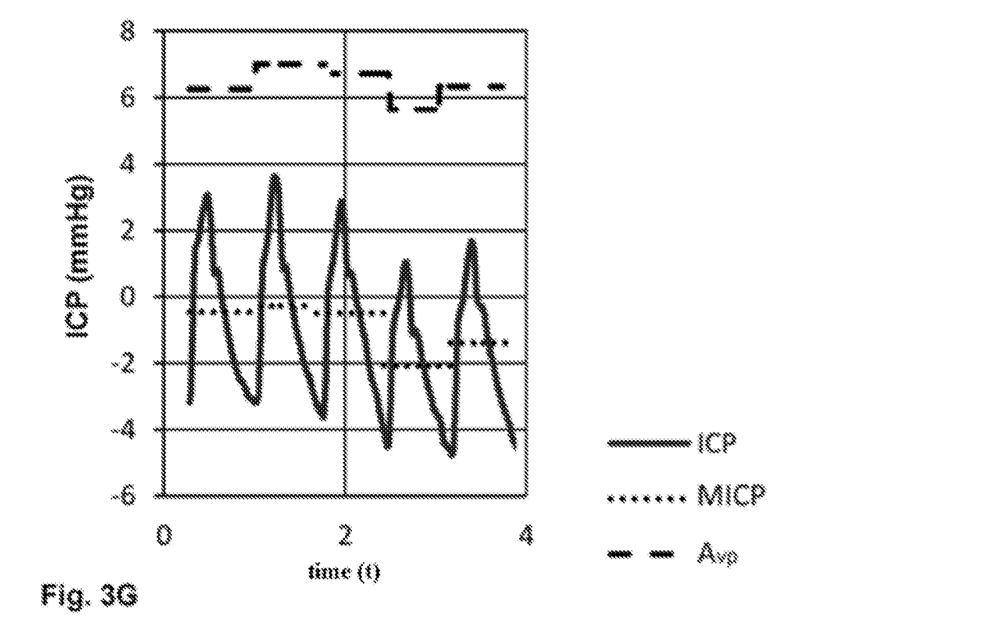
Figure 3H:
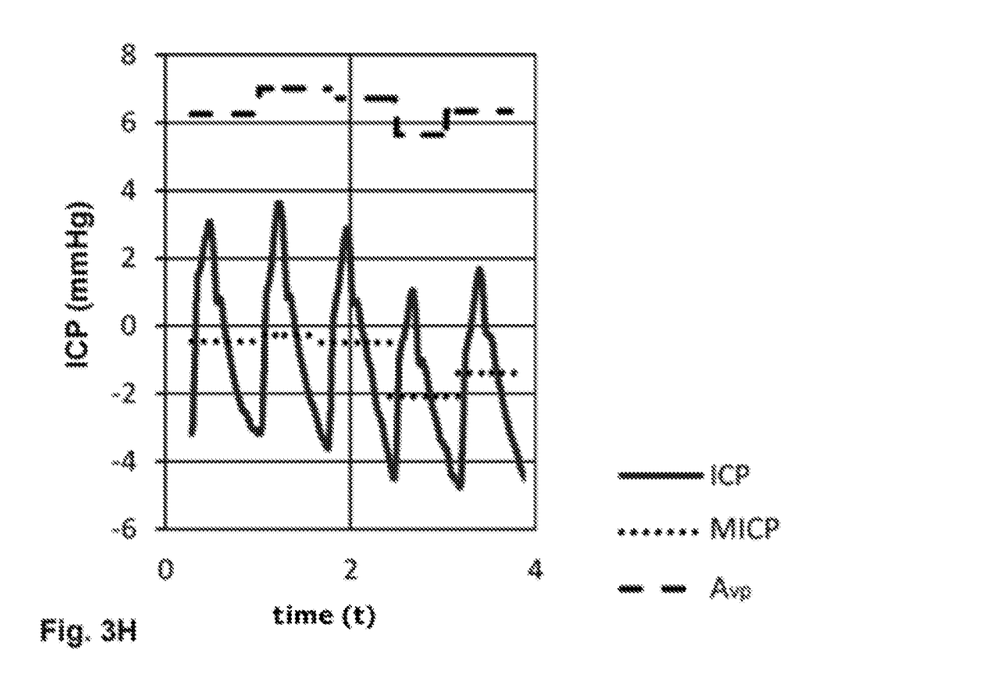
Figure 3I:
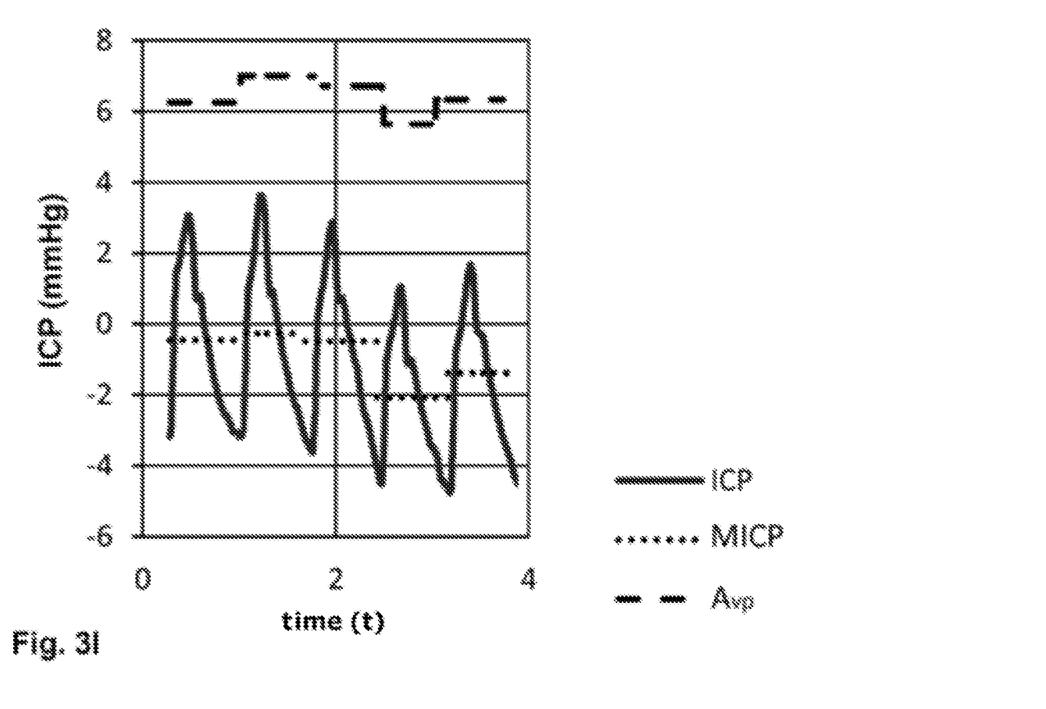

FIG. 3A shows first a period of the pressure signal ICP. It can be seen in FIG. 3B how to calculate the mean value MICP of the period of ICP shown. Further, FIG. 3C shows how the pulse amplitude $A_{vp}$ can be calculated, for example by forming a difference between the local maximum MAX of ICP and the first local minimum MIN1 of ICP for the time period T1 between the first local minimum MIN1 of ICP and the first local maximum MAX of ICP ($A_{vp}$(T1)=MAX−MIN1). For the second time period T2 between the local maximum MAX of ICP and the second local minimum MIN2 of ICP, for $A_{vp}$ the difference between the local maximum MAX of ICP and the second minimum MIN2 of ICP can be set accordingly (i.e. $A_{vp}$(T2)=MAX−MIN2). Analogously, then MICP is also determined separately for the half periods T1 and T2 as the average pressure between MIN1 and MAX and between MAX and MIN2. This can be continued in the other periods of ICP shown in FIGS. 3D through 3I. By analogy, $A_{vp}$ and MICP may each be determined as "half periods" between local minimum and local maximum as the first half period and between local maximum and next local minimum as the second half period, or they may each be determined for whole periods.

Figure 3J:
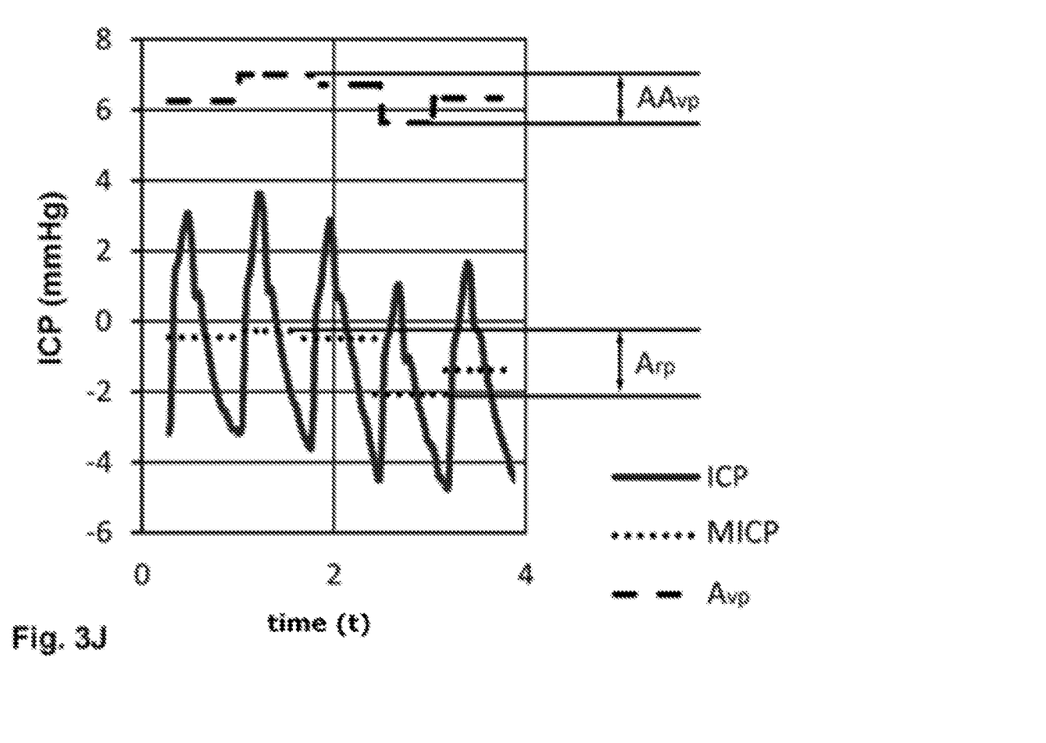

FIG. 3J then shows by way of example the calculation of the amplitude $AA_{vp}$ from the time series $A_{vp}$ and the calculation of the amplitude Arp from the time series MICP. Here, $AA_{vp}$ results in the difference between the maximum and the minimum of the time series $A_{vp}$. Furthermore, Arp is the difference between the maximum and the minimum of the time series MICP.

The resulting value RAQ is dimensionless and independent of the calibration and the transmission factor of the characteristic signal obtained. Therefore, it is particularly suitable for use with noninvasively obtained signals whose calibration and transmission factors are unknown.

In a preferred embodiment of the invention, the processing described above is performed by one or more analog computing circuits.

In a further preferred embodiment of the invention, the evaluation is performed by one or more digitally operating arithmetic circuits.

In a particularly preferred embodiment of the invention, the evaluation is performed by one or more computers or microprocessor circuits controlled by one or more programs. Furthermore, the calculation of the pulse amplitude described under a) and the signals or time series described under a) and b) are performed by an algorithm in the time domain. The calculation of the amplitudes described under c) and d) is preferably carried out by determining the maxima and minima in the time series $A_{vp}$ and $AA_{rp}$ and forming the differences between successive maxima and minima.

The calculation of the amplitudes described under c) and d) is particularly preferably carried out by calculating the amplitude spectra of the time series Avp and $AA_{rp}$ and determining the maxima in the range of the respiratory frequency.

In a further particular embodiment of the invention, two devices according to the invention for different combinations of modulated and modulating wave are present and the characteristic parameter is calculated by calculating the quotient of the output value or the output signal of the first device and the output value or the output signal of the second device. Preferably, in the first device, the signal RAQ1 is calculated with the respiratory wave as the modulating wave and the heartbeat-related pulse wave as the modulated wave, in the second device the signal RAQ2 is calculated with the B-wave as a modulating wave and the heartbeat-related pulse wave as a modulated wave. The characteristic parameter is then calculated as the quotient RAQ1/RAQ2 or its reciprocal.

In the following, further aspects and embodiments of the present invention are presented in the form of points which can also be formulated as claims. The reference numbers refer to the figures.

Point 1: Device for determining a characteristic parameter of the head content of humans and other mammals characterized by obtaining and processing of a signal characteristic of the head content as an input variable with units for
- a. Calculation of the pulse amplitude $A_{vp}$ of each individual period of a modulated wave and generation of a signal or time series $A_{vp}$ (3),
- b. calculation of the average value MICP for each individual period of the modulated wave and generation of a signal or time series MICP (4),
- c. calculation of the amplitude $A_{rp}$ of a modulating wave in the time series MICP (5),
- d. calculation of the amplitude $AA_{vp}$ of the modulating wave in the time series $A_{vp}$ (6),
- e. calculation of the quotient $RAQ=A_{rp}/AA_{vp}$ (7) as output value.

Point 2: Device according to the preceding point, wherein the characteristic signal is the directly measured pressure inside the head.

Point 3: Device according to one or more of the preceding points, wherein the characteristic signal is the electrical impedance of the skull, which is obtained by external electrodes attached to the skull.

Point 4: Device according to one or more of the preceding points, wherein the characteristic signal is the electrical capacitance of the skull, which is obtained by external electrodes attached to the skull.

Point 5: Device according to one or more of the preceding points, wherein the characteristic signal is the transit time of an ultrasound signal, which is passed through the skull.

Point 6: Device according to one or more of the preceding points, wherein the characteristic signal is the transit time of an ultrasound signal that is reflected from the interior of the skull.

Point 7: Device according to one or more of the preceding points, wherein one or more of the units for the
- a. calculation of the pulse amplitude $A_{vp}$ of each individual period of the modulated wave and generation of a signal or a time series $A_{vp}$ (3),
- b. calculation of the average value MICP for each individual period of the modulated wave and generation of a signal or time series MICP (4).
- c. calculation of the amplitude $A_{rp}$ of the modulating wave in the signal of time series MICP (5),
- d. calculation of the amplitude $AA_{vp}$ of the modulating wave in the signal or time series $A_{vp}$ (6),
- e. calculation of the quotient $RAQ=A_{rp}/AA_{vp}$ (7) as output value are analog computing circuits.

Point 8: Device according to one or more of the preceding points, wherein one or more of the units for the
- a. calculation of the pulse amplitude $A_{vp}$ of each individual period of the modulated wave and generation of a signal or a time series $A_{vp}$ (3),
- b. calculation of the average value MICP for each individual period of the modulated wave and generation of a signal or time series MICP (4).
- c. calculation of the amplitude $A_{rp}$ of the modulating wave in the signal of time series MICP (5),
- d. Calculation of the amplitude $AA_{vp}$ of the modulating wave in the signal or time series $A_{vp}$ (6),
- e. calculation of the quotient $RAQ=A_{rp}/AA_{vp}$ (7) as output value are digital arithmetic circuit.

Point 9: Device according to one or more of the preceding points, wherein one or more of the units for the
- a. calculation of the pulse amplitude $A_{vp}$ of each individual period of the modulated wave and generation of a signal or a time series $A_{vp}$ (3),
- b. calculation of the average value MICP for each individual period of the modulated wave and generation of a signal or time series MICP (4),
- c. calculation of the amplitude $A_{rp}$ of the modulating wave in the signal of time series MICP (5),
- d. calculation of the amplitude $AA_{vp}$ of the modulating wave in the signal or time series $A_{vp}$ (6),
- e. calculation of the quotient $RAQ=A_{rp}/AA_{vp}$ (7) as output value are programmable computers or microprocessor circuits.

Point 10: Device according to one or more of the preceding points, wherein the modulated wave is one of the periodic waves from the group of B-waves (⅓ per min to 3 per min), C-waves (3 per min to 9 per min), respiratory waves (10 per min to 20 per min), heartbeat induced waves (20 per min to 240 per min).

Point 11: Device according to one or more of the preceding points, wherein the modulating wave is one of the periodic waves from the group of A-waves (<1 per 4 min), B-waves (⅓ per min to 3 per min), C waves (3 per minute to 9 per minute), respiratory waves (10 per minute to 20 per minute), which has a lower frequency than the modulated wave.

Point 12: Device for determining a characteristic parameter of the head content of humans and other mammals characterized by obtaining and processing a signal characteristic of the head characterized by a combination of a first device according to one or more of the preceding points and a second device according to one or more of the preceding points, characterized in that the first device is characterized by a certain combination of modulated and modulating wave and that the second device is characterized by a different combination of modulated and modulating wave and that the characteristic parameter of the head content is formed as the quotient of the output signal or the output value of the first device and the output signal or the output value of the second device.

BIBLIOGRAPHY

[1] S. Jetzki, M. Kiefer, R. Eymann, M. Walter, and S. Leonhardt, "Analysis of pulse waves in intracranial pressure" in Conference proceedings: Annual International Conference of the IEEE Engineering in Medicine and Biology Society. IEEE Engineering in Medicine and Biology Society. Conference, 2006, vol. 2007, pp. 2863-2866.

[2] D. J. Price, M. Czosnyka, and M. Williamson, "Attempts to continuously monitor autoregulation and compensatory reserve in severe head injuries," in Intracranial Pressure VIII, Springer, 1993, pp. 61-66,

[3] M. Czosnyka, Z. Czosnyka, N. Keong, A. Lavinio, P. Smielewski, S. Momjian, E. A. Schmidt, G. Petrella, B.

Owler, and J. D. Pickard, "Pulse pressure waveform in hydrocephalus: what it is and what it isn't," Neurosurg. Focus, vol. 22, no. 4, pp. 1-7, 2007.

[4] N. Lenfeldt, N. Andersson, A. Agren-Wilsson, A. T. Bergenheim, L.-O. D. Koskinen, A. Eklund, and J. Maim, "Cerebrospinal fluid pulse pressure method: a possible substitute for the examination of B waves," J. Neurosurg., vol. 101, no. 6, pp. 944-950, 2004.

The invention claimed is:

1. A device for diagnostics of hydrocephalus, comprising:
a microprocessor circuit,;
a memory operatively connected to the microprocessor circuit and storing a computer program, wherein the computer program comprises instructions that, when executed by the microprocessor circuit cause the device to:
a. access a stored characteristic signal that is characteristic of the head content of a human or mammal and is the electrical impedance of the skull,
b. calculate the pulse amplitude of each individual period or half period of a modulated wave of the characteristic signal and to generate a signal $A_{vp}$ or a time series $A_{vp}$ comprising the pulse amplitudes,
c. calculate the mean value for each single period or half period of the modulated wave of the characteristic signal and generate a signal MICP or a time series MICP comprising the mean values,
d. calculate the amplitude $A_{rp}$ of a modulating wave in the time series MICP or in the signal MICP,
e. calculate the amplitude $AA_{vp}$ of the modulating wave in the time series $A_{vp}$ or in the signal $A_{vp}$,
f. calculate a characteristic parameter as an output value being indicative of hydrocephalus, wherein the characteristic parameter is a quotient comprising the amplitudes $A_{rp}$ and $AA_{vp}$, and wherein the modulated wave is one of the following waves: a periodic wave from the group of B-waves or C-waves, a respiratory wave, a heartbeat-induced wave; and wherein the modulating wave is one of the following waves: a periodic wave from the group of A-waves, a periodic wave from the group of B-waves, a periodic wave from the group of C-waves, a respiratory wave, wherein the modulating wave has a lower frequency than the modulated wave.

2. Device according to claim 1, characterized in that the characteristic parameter is a dimensionless parameter.

3. Device according to claim 1, characterized in that the characteristic parameter is a quotient comprising at least one of the quantities HF, AF, where HF is the heart rate and AF is the respiratory rate.

4. Device according to claim 1, characterized in that the quotient (RAQ) is proportional to or equal to one of the following expressions: $A_{rp}/AA_{vp}$, $A_{rp}/(AA_{vp}/AF)$, $A_{rp}/(AA_{vp}*HF)$, $A_{rp}/(AA_{vp}*(HF/AF))$,
wherein HF is the heart rate and AF is the respiratory rate.

5. A device for diagnostics of hydrocephalus, comprising:
a microprocessor circuit;
a memory operatively connected to the microprocessor circuit and storing a computer program, wherein the computer program comprises instructions that, when executed by the microprocessor circuit cause the device to:
a. access a stored characteristic signal that is characteristic of the head content of a human or mammal and is a pressure directly measured in the head,
b. calculate the pulse amplitude of each individual period or half period of a modulated wave of the characteristic signal and to generate a signal $A_{vp}$ or a time series $A_{vp}$ comprising the pulse amplitudes,
c. calculate the mean value for each single period or half period of the modulated wave of the characteristic signal and generate a signal MICP or a time series MICP comprising the mean values,
d. calculate the amplitude $A_{rp}$ of a modulating wave in the time series MICP or in the signal MICP,
e. calculate the amplitude $AA_{vp}$ of the modulating wave in the time series $A_{vp}$ or in the signal $A_{vp}$,
f. calculate a characteristic parameter as an output value being indicative of hydrocephalus, wherein the characteristic parameter is a quotient comprising the amplitudes $A_{rp}$ and $AA_{vp}$, and wherein the modulated wave is one of the following waves: a periodic wave from the group of B-waves or C-waves, a respiratory wave, a heartbeat-induced wave; and wherein the modulating wave is one of the following waves: a periodic wave from the group of A-waves, a periodic wave from the group of B-waves, a periodic wave from the group of C-waves, a respiratory wave, wherein the modulating wave has a lower frequency than the modulated wave.

6. A device for diagnostics of hydrocephalus, comprising:
a microprocessor circuit;
a memory operatively connected to the microprocessor circuit and storing a computer program, wherein the computer program comprises instructions that, when executed by the microprocessor circuit cause the device to:
a. access a stored characteristic signal that is characteristic of the head content of a human or mammal and is the transit time of an ultrasonic signal which is passed through the skull or is reflected from the interior of the skull,
b. calculate the pulse amplitude of each individual period or half period of a modulated wave of the characteristic signal and to generate a signal $A_{vp}$ or a time series $A_{vp}$ comprising the pulse amplitudes,
c. calculate the mean value for each single period or half period of the modulated wave of the characteristic signal and generate a signal MICP or a time series MICP comprising the mean values,
d. calculate the amplitude $A_{rp}$ of a modulating wave in the time series MICP or in the signal MICP,
e. calculate the amplitude $AA_{vp}$ of the modulating wave in the time series $A_{vp}$ or in the signal $A_{vp}$,
f. calculate a characteristic parameter as an output value being indicative of hydrocephalus, wherein the characteristic parameter is a quotient comprising the amplitudes $A_{rp}$ and $AA_{vp}$, and wherein the modulated wave is one of the following waves: a periodic wave from the group of B-waves or C-waves, a respiratory wave, a heartbeat-induced wave; and wherein the modulating wave is one of the following waves: a periodic wave from the group of A-waves, a periodic wave from the group of B-waves, a periodic wave from the group of C-waves, a respiratory wave, wherein the modulating wave has a lower frequency than the modulated wave.

7. Device according to claim 5, characterized in that the characteristic parameter is a dimensionless parameter.

8. Device according to claim 5, characterized in that the characteristic parameter is a quotient comprising at least one of the quantities HF, AF, where HF is the heart rate and AF is the respiratory rate.

9. Device according to claim 5, characterized in that the quotient (RAQ) is proportional to or equal to one of the following expressions: $A_{rp}/AA_{vp}$, $A_{rp}/(AA_{vp}/AF)$, $A_{rp}/$ $(AA_{vp} * HF)$, $A_{rp}/(AA_{vp} * (HF/AF))$), wherein HF is the heart rate and AF is the respiratory rate.

10. Device according to claim 6, characterized in that the characteristic parameter is a dimensionless parameter.

11. Device according to claim 6, characterized in that the characteristic parameter is a quotient comprising at least one of the quantities HF, AF, where HF is the heart rate and AF is the respiratory rate.

12. Device according to claim 6, characterized in that the quotient (RAQ) is proportional to or equal to one of the following expressions: $A_{rp}/AA_{vp}$, $A_{rp}/(AA_{vp}/AF)$, $A_{rp}/(AA_{vp} * HF)$, $A_{rp}/(AA_{vp} * (HF/AF))$, wherein HF is the heart rate and AF is the respiratory rate.

* * * * *